United States Patent
Takahashi

(10) Patent No.: US 12,430,761 B2
(45) Date of Patent: Sep. 30, 2025

(54) SERVER APPARATUS, SYSTEM, CONTROL METHOD OF SERVER APPARATUS, AND STORAGE MEDIUM

(71) Applicant: NEC Corporation, Tokyo (JP)

(72) Inventor: Yusuke Takahashi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 328 days.

(21) Appl. No.: 18/036,365

(22) PCT Filed: Nov. 18, 2020

(86) PCT No.: PCT/JP2020/042922
§ 371 (c)(1),
(2) Date: May 10, 2023

(87) PCT Pub. No.: WO2022/107232
PCT Pub. Date: May 27, 2022

(65) Prior Publication Data
US 2024/0013376 A1 Jan. 11, 2024

(51) Int. Cl.
*G06K 9/00* (2022.01)
*A61B 5/00* (2006.01)
(Continued)

(52) U.S. Cl.
CPC .......... *G06T 7/0012* (2013.01); *A61B 5/0008* (2013.01); *A61B 5/015* (2013.01);
(Continued)

(58) Field of Classification Search
CPC ............. G06T 7/00; G06K 9/00; A61K 35/12
(Continued)

(56) References Cited

U.S. PATENT DOCUMENTS

2018/0061159 A1* 3/2018 Saso ................. G07C 9/37
2021/0304584 A1* 9/2021 Singh ................. G01J 5/07
(Continued)

FOREIGN PATENT DOCUMENTS

JP 2012-235415 A 11/2012
JP 2013-172932 A 9/2013
(Continued)

OTHER PUBLICATIONS

Technologies for Fever Screening in the Time of COVID-19: A Review Scott D. Adams, Member, IEEE, Andrew Valentine, Tracey K. Bucknall, and Abbas Z. Kouzani, Member, IEEE (Year: 2022).*

(Continued)

*Primary Examiner* — Seyed H Azarian

(57) ABSTRACT

A server apparatus includes registration unit, detection unit, and notification unit. The registration unit acquires thermal image data representing thermal distribution of first location and first image data from first camera device. The registration unit determines whether or not first person passing through the first place is person with fever based on thermal image data. The registration unit acquires biometric information of the person with fever from the first image data and registers the biometric information of the person with fever in database. The detection unit acquires second image data photographed at second location from second camera device. The detection unit detects person with fever at second location using biometric information of second person in the second image data and the biometric information registered in the database. The notification unit transmits fever detection notification to terminal owned by staff member to guide the person with fever to third location.

11 Claims, 16 Drawing Sheets

(51) Int. Cl.
  *A61B 5/01* (2006.01)
  *A61B 5/1171* (2016.01)
  *A61K 35/12* (2015.01)
  *G06T 7/00* (2017.01)
  *G06V 40/16* (2022.01)
  *G06V 40/50* (2022.01)
  *G07C 9/10* (2020.01)
  *G07C 9/38* (2020.01)

(52) U.S. Cl.
  CPC .............. *A61B 5/1176* (2013.01); *G06T 7/97* (2017.01); *G06V 40/173* (2022.01); *G06V 40/50* (2022.01); *G07C 9/10* (2020.01); *G07C 9/38* (2020.01); *G06T 2207/10048* (2013.01); *G06T 2207/30201* (2013.01); *G06T 2207/30232* (2013.01)

(58) Field of Classification Search
  USPC ........ 382/100, 103, 106–107, 115–118, 156, 382/162, 168, 173, 181, 199, 220, 224, 382/254, 276, 286–291, 305; 348/47, 71
  See application file for complete search history.

(56) References Cited

U.S. PATENT DOCUMENTS

| | | | |
|---|---|---|---|
| 2021/0345885 A1* | 11/2021 | Umeda | A61B 5/01 |
| 2023/0222832 A1* | 7/2023 | Kochi | G06V 40/168 382/118 |
| 2023/0308303 A1* | 9/2023 | Jorasch | H04L 65/4015 |
| 2025/0160668 A1* | 5/2025 | Frank | A61B 5/02141 |

FOREIGN PATENT DOCUMENTS

| | | |
|---|---|---|
| JP | 2018-037075 A | 3/2018 |
| JP | 2019-083395 A | 5/2019 |
| JP | 2020-035114 A | 3/2020 |
| JP | 2020-120323 A | 8/2020 |
| WO | 2017/057274 A1 | 4/2017 |
| WO | 2020/050397 A1 | 3/2020 |

OTHER PUBLICATIONS

International Search Report for PCT Application No. PCT/JP2020/042922, mailed on Feb. 2, 2021.

* cited by examiner

FIG. 4

FEVER INFORMATION DATABASE

| FEVER ID | FEATURE VALUE | FACE IMAGE | BODY SURFACE TEMPERATURE | ... |
|---|---|---|---|---|
| ID01 | Fv01 | F01 | T1 | ... |
| ID02 | Fv02 | F02 | T2 | ... |
| ID03 | Fv03 | F03 | T3 | ... |
| ID04 | Fv04 | F04 | T4 | ... |
| ... | ... | ... | ... | ... |

FIG. 11

FEVER LIST

| No | FEATURE VALUE |
|----|---------------|
| 01 | Fv01 |
| 02 | Fv02 |
| 03 | Fv03 |
| 04 | Fv04 |
| ... | ... |

FIG. 16

FEVER INFORMATION DATABASE

| FEVER ID | FEATURE VALUE | FACE IMAGE | BODY SURFACE TEMPERATURE | DETECTION STATUS | |
|---|---|---|---|---|---|
| ID01 | Fv01 | F01 | T1 | DONE | ... |
| ID02 | Fv02 | F02 | T2 | DONE | ... |
| ID03 | Fv03 | F03 | T3 | — | ... |
| ID04 | Fv04 | F04 | T4 | — | ... |
| ... | ... | ... | ... | ... | ... |

SERVER APPARATUS, SYSTEM, CONTROL METHOD OF SERVER APPARATUS, AND STORAGE MEDIUM

This application is a National Stage Entry of PCT/JP2020/042922 filed on Nov. 18, 2020, the contents of all of which are incorporated herein by reference, in their entirety.

TECHNICAL FIELD

The present invention relates to a server apparatus, a system, a control method of a server apparatus, and a storage medium.

BACKGROUND ART

There exists a technology to detect a person with fever among a large number of users of facilities such as airports. For example, Patent Literature 1 describes that it is provided an information processing device and matching method that are capable of properly detecting a person with fever using a thermal camera, even when there are many users of a facility.

CITATION LIST

Patent Literature

[PTL 1] Japanese Unexamined Patent Application Publication No. 2020-120323

SUMMARY OF INVENTION

Technical Problem

It is important to detect an unwell person during an epidemic of an infectious disease and to inspect whether or not the unwell person is suffering from the infectious disease. In this regard, the technology disclosed in Patent Literature 1 is limited to detecting a person with fever among airport users, and there is no mention of inspection of a person with fever.

It is a main object of the present invention to provide a server apparatus, a system, a method of controlling a server apparatus, and a storage medium that contribute to carrying out an inspection of an unwell person.

Solution to Problem

According to a first aspect of the present invention, there is provided a server apparatus, including: a registration unit that acquires thermal image data representing a thermal distribution of a first location and first image data photographed at the first location from a first camera device installed at the first location, determines whether or not a first person passing through the first location is a person with fever based on the thermal image data, acquires biometric information of the person with fever from the first image data, and registers the biometric information of the person with fever in a fever information database; a detection unit that acquires second image data photographed at a second location from a second camera device installed at the second location, and detects the person with fever at the second location using biometric information of a second person in the second image data and the biometric information registered in the fever information database; and a notification unit that transmits a fever detection notification, the fever detection notification including biometric information of the detected person with fever, to a terminal owned by a staff member to guide the person with fever to a third location.

According to a second aspect of the present invention, there is provided a system including: a first camera device installed at a first location; a second camera device installed at a second location; a terminal owned by a staff member; and a server apparatus connected to the first camera device, the second camera device and the terminal, wherein the server apparatus includes: a registration unit that acquires thermal image data representing a thermal distribution of a first location and first image data photographed at the first location from a first camera device installed at the first location, determines whether or not a first person passing through the first location is a person with fever based on the thermal image data, acquires biometric information of the person with fever from the first image data, and registers the biometric information of the person with fever in a fever information database; a detection unit that acquires second image data photographed at the second location from the second camera device, and detects the person with fever at the second location using biometric information of a second person in the second image data and the biometric information registered in the fever information database; and a notification unit that transmits a fever detection notification, the fever detection notification including biometric information of the detected person with fever, to a terminal owned by a staff member to guide the person with fever to a third location.

According to a third aspect of the present invention, there is provided a control method of a server apparatus, the control method including: acquiring thermal image data representing a thermal distribution of a first location and first image data photographed at the first location from a first camera device installed at the first location; determining whether or not a first person passing through the first location is a person with fever based on the thermal image data; acquiring biometric information of the person with fever from the first image data, and registering the biometric information of the person with fever in a fever information database; acquiring second image data photographed at a second location from a second camera device installed at the second location; detecting the person with fever at the second location using biometric information of a second person in the second image data and the biometric information registered in the fever information database; and transmitting a fever detection notification, the fever detection notification including biometric information of the detected person with fever, to a terminal owned by a staff member to guide the person with fever to a third location.

According to a fourth aspect of the present invention, there is provided a computer-readable storage medium storing a program causing a computer mounted on a server apparatus to perform processing for: acquiring thermal image data representing a thermal distribution of a first location and first image data photographed at the first location from a first camera device installed at the first location; determining whether or not a first person passing through the first location is a person with fever based on the thermal image data; acquiring biometric information of the person with fever from the first image data, and registering the biometric information of the person with fever in a fever information database; acquiring second image data photographed at a second location from a second camera device installed at the second location; detecting the person with fever at the second location using biometric information of a second person in the second image data and the biometric information registered in the fever information database; and transmitting a fever detection notification, the fever detection notification including biometric information of the detected person with fever, to a terminal owned by a staff member to guide the person with fever to a third location.

Advantageous Effects of Invention

The individual aspects of the present invention provide a server apparatus, a system, a control method of a server apparatus, and a storage medium that contribute to carrying out an inspection of an unwell person. The advantageous effect of the present invention is not limited to the above advantageous effect. The present invention may provide other advantageous effects, instead of or in addition to the above advantageous effect.

BRIEF DESCRIPTION OF THE DRAWINGS

FIG. 4 is a diagram illustrating an example of a fever information database according to the first example embodiment.

FIG. 11 is a diagram illustrating an example of a fever list according to the third example embodiment.

FIG. 16 is a diagram illustrating an example of a fever information database according to a variation in the present application.

EXAMPLE EMBODIMENT

Figure 1:
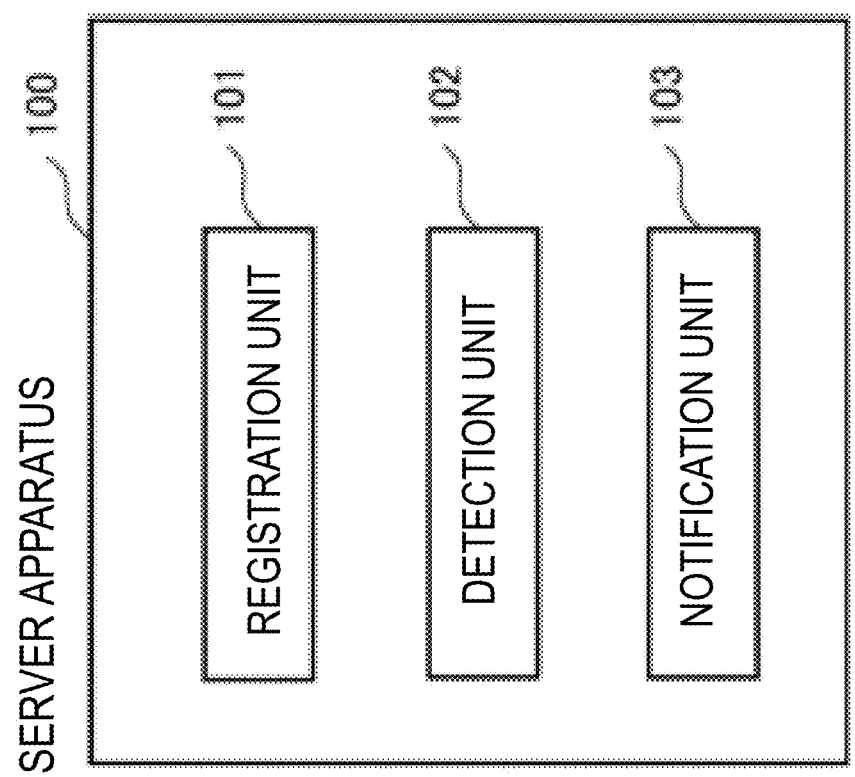
FIG. 1 is a diagram illustrating an outline of an example embodiment.

First, an outline of an example embodiment will be described. In the following outline, various components are denoted by reference characters for the sake of convenience. That is, the following reference characters are used as examples to facilitate the understanding of the present invention. Thus, the description of the outline is not intended to impose any limitations. In addition, unless otherwise specified, an individual block illustrated in the drawings represents a configuration of a functional unit, not a hardware unit. An individual connection line between blocks in the drawings signifies both one-way and two-way directions. An arrow schematically illustrates a principal signal (data) flow and does not exclude bidirectionality. In the present description and drawings, elements that can be described in a like way will be denoted by a like reference character, and redundant description thereof will be omitted as needed.

A server apparatus 100 according to an example embodiment includes a registration unit 101, a detection unit 102, and a notification unit 103 (see FIG. 1). The registration unit 101 acquires thermal image data representing a thermal distribution of a first location and first image data photographed at the first location from a first camera device installed at the first location. The registration unit 101 determines whether or not a first person passing through the first location is a person with fever based on the thermal image data. The registration unit 101 acquires biometric information of the person with fever from the first image data and registers the biometric information of the person with fever in a fever information database. The detection unit 102 acquires second image data photographed at a second location from a second camera device installed at the second location. The detection unit 102 detects the person with fever at the second location using biometric information of a second person in the second image data and the biometric information registered in the fever information database. The notification unit 103 transmits a fever detection notification, the fever detection notification including biometric information of the detected person with fever, to a terminal owned by a staff member to guide the person with fever to a third location.

The server apparatus 100 analyzes the thermal image data and registers biometric information of a person with fever whose body surface temperature is greater than a predetermined value with a system. The server apparatus 100 determines whether or not a photographed person in the image data photographed by the second camera device is the person with fever registered in the system. The server apparatus 100 transmits the fever detection notification including biometric information of the person with fever to the terminal owned by the staff member. The staff member goes to the person with fever (the unwell person) relying on the face image of the person with fever displayed on the terminal and guides the person with fever to an inspection room. As a result, the staff member can easily locate the person with fever and carry out an inspection of the person with fever.

Hereinafter, specific example embodiments will be described in more detail with reference to drawings.

First Example Embodiment

A first example embodiment will be described in more detail with reference to drawings.

[System Configuration]

Figure 2:
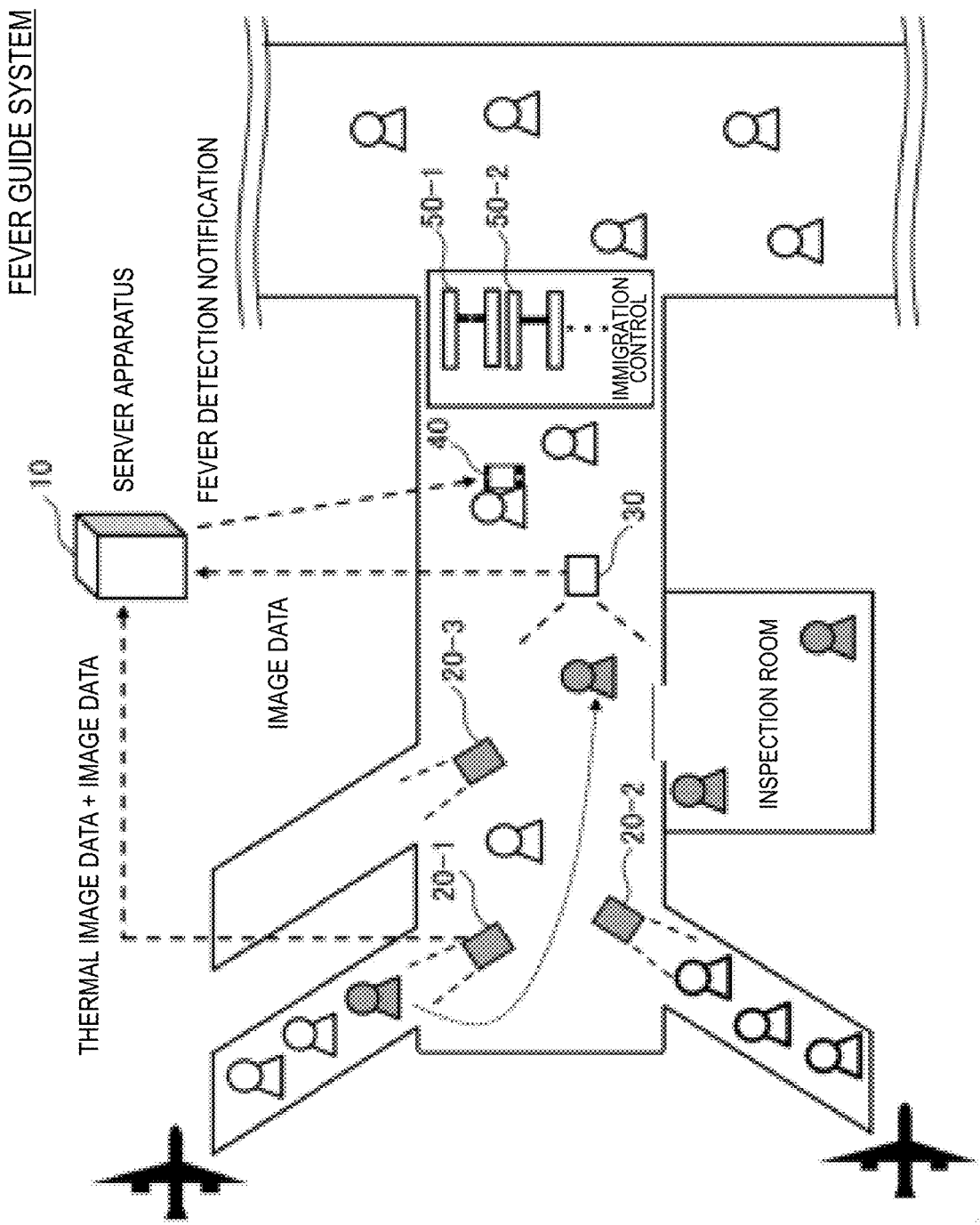
FIG. 2 is a diagram illustrating an example of an example of a schematic configuration of a fever guide system according to a first example embodiment.

FIG. 2 is a diagram illustrating an example of a schematic configuration of a fever guide system according to a first example embodiment. The fever guide system of the first example embodiment is a system that detects an unwell person among passengers and guides the unwell person to an inspection room. The fever guide system shown in FIG. 2 is operated, for example, by a public organization such as an entry/departure control bureau or a trustee entrusted by such a public organization.

The first example embodiment describes a case where an unwell person is detected between the time a passenger disembarks from an aircraft and immigration examination. The first example embodiment describes a case where an unwell person (a person with fever) is detected among passengers entering a country from a foreign country, but the unwell person may also be detected among passengers moving within the country.

Referring to FIG. 2, the fever guide system includes a server apparatus 10, first camera devices 20-1 to 20-3, and a second camera device 30.

In the following description, unless there is a particular reason to distinguish first camera devices 20-1 to 20-3 from each other, any one of these first camera devices 20-1 to 10-3 will simply be referred to as "first camera device 20". Other configurations are similarly represented by the sign to the left of the hyphen.

The server apparatus 10 is an apparatus that controls the entire fever guide system. The server apparatus 10 is installed in a facility at an airport. Alternatively, the server apparatus 10 may be a server located in a cloud on a network.

A first camera device 20 is installed at a first location in an airport. More specifically, the first camera device 20 is installed on a wall or ceiling in an airport terminal near where an airplane arrives. The first camera device 20 is installed to be able to photograph passengers disembarking from the airplane. For example, the first camera device 20 is installed to be able to photograph passengers passing through a narrow corridor that connects a runway where the airplane lands and the airport terminal. With such an installation mode, the first camera device 20 basically photographs one person.

The first camera device 20 acquires image data representing a heat distribution at the first location and image data (image data representing a distribution of light reflected off objects) photographed at the first location. That is, the first camera device 20 has two functions as a thermal camera and infrared camera capable of acquiring a body surface temperature of the photographed person (passenger), and as a standard camera capable of acquiring normal image data. That is, the first camera device 20 is a camera device capable of acquiring infrared image and visible light image. The infrared image is used to measure the body surface temperature of the photographed person, and the visible light image is used to acquire face feature value of the photographed person.

The first camera device 20 acquires image data that includes information regarding a body surface temperature of a subject and acquires image data in which the subject appears. The first camera device 20 acquires the two pieces of image data at substantially the same timing. The first camera device 20 transmits the acquired two types of image data to the server apparatus 10.

In the following description, image data including a thermal distribution (a human body surface temperature) is referred to as "thermal image data". Normal image data in which a subject is photographed is referred to as "normal image data" or simply "image data".

Note that a photographable range and a temperature measurable range of the first camera device 20 are set substantially the same. That is, an angle of view of a thermal camera and a standard camera are substantially the same. In addition, the photographable range and the temperature measurable range of the first camera device 20 are set narrow. The ranges are narrow because there is a trade-off between an accuracy of a thermal measurement and a distance between a photographed person and a camera.

The second camera device 30 is installed at a second location. More specifically, the second camera device 30 is installed on a wall or ceiling in an airport terminal. The second camera device 30 is installed to be able to photograph passengers heading to a quarantine area (not shown) or an immigration examination area (an immigration control). A plurality of gate apparatuses 50 are installed in the immigration examination area and an immigration examination is carried out at the gate apparatuses 50.

The second camera device 30 acquires normal image data and transmits the image data to the server apparatus 10. The second camera device 30 transmits image data (normal image data) that it photographed the second location to the server apparatus 10.

A photographable range of the second camera device 30 can be set wider than the photographable range of the first camera device 20. This is because the second camera device 30 does not acquire thermal image data.

In the drawings including FIG. 2, gray-colored persons indicate unwell persons (persons with fever).

Each of devices shown in FIG. 2 is connected to the server apparatus 10 via a network (not shown). The network consists of LAN (Local Area Network), WAN (Wide Area Network), mobile communication network, and so on including a premises communication network of an airport. A connection method is not limited to a wired method and may be a wireless method.

The configuration shown in FIG. 2 is an example and is not intended to limit a configuration of the fever guide system. The fever guide system may include a terminal and so on which are not shown. For example, the fever guide system may include a digital signage and so on for providing information to passengers. In addition, while three first camera devices 20 and one second camera device 30 are illustrated in FIG. 2, the number of camera devices included in the system is not of course limited to any particular number.

[Schematic Operation of System]

Next, a schematic operation of the fever guide system will be described with reference to the drawings.

The first camera device 20 acquires thermal image data and normal image data periodically or at predetermined timings. The first camera device 20 photographs a passenger disembarking from an airplane and moving to an airport terminal. The first camera device 20 transmits image data including a face image of the passenger and thermal image data including information on a body surface temperature of the passenger to the server apparatus 10.

The server apparatus 10 analyzes the thermal image data to determine whether or not a subject (a photographed person) has a fever. When the photographed person has fever, the server apparatus 10 extracts a face image from acquired image data. The server apparatus generates feature value from the extracted face image. The server apparatus 10 stores the face image of the person with fever, the generated feature value, and the body surface temperature in a fever information database in correspondence.

The second camera device 30 acquires normal image data periodically or at predetermined timings. The second camera device 30 photographs passengers walking through the airport terminal. The second camera device 30 transmits image data including the face image of the passenger to the server apparatus 10.

The server apparatus 10 extracts a face image from the image data acquired from the second camera device 30. The server apparatus 10 generates feature value from the extracted face image. The server apparatus 10 performs 1-to-N matching (N is a positive integer, and the same applies to the following description) by setting the generated feature value to a matching side and the feature values registered in the fever information database to a registration side, respectively.

When the matching fails (the photographed person by the second camera device 30 is not registered in the fever information database), the server apparatus 10 does not take any particular operation.

When the matching is successful (when the photographed person by the second camera device 30 is registered in the fever information database), the server apparatus 10 transmits a "fever detection notification" to a terminal 40 owned by a staff member in an airport to guide the person with fever to an inspection room (a third location). The fever detection notification includes biometric information (a face image) of the person with fever. The terminal 40 displays the face image.

The staff member locates the person with fever walking through the airport terminal referring to the face image displayed on the terminal 40. Since the person with fever is being photographed by the second camera device 30, the staff member searches for the person with fever near an installation position of the second camera device 30. Once the staff member locates the person with fever, the staff member guides the person with fever to an inspection room (asks the person with fever to move to the inspection room).

In the inspection room, an inspection is carried out to determine whether or not the person with fever has an infectious disease and so on. The inspection room is an isolated room where an unwell person (a person with fever) is inspected (e.g., an inspection to determine whether or not the unwell person has an infectious disease).

Next, details of each device included in the fever guide system according to the first example embodiment will be described.

[Server Apparatus]

Figure 3:
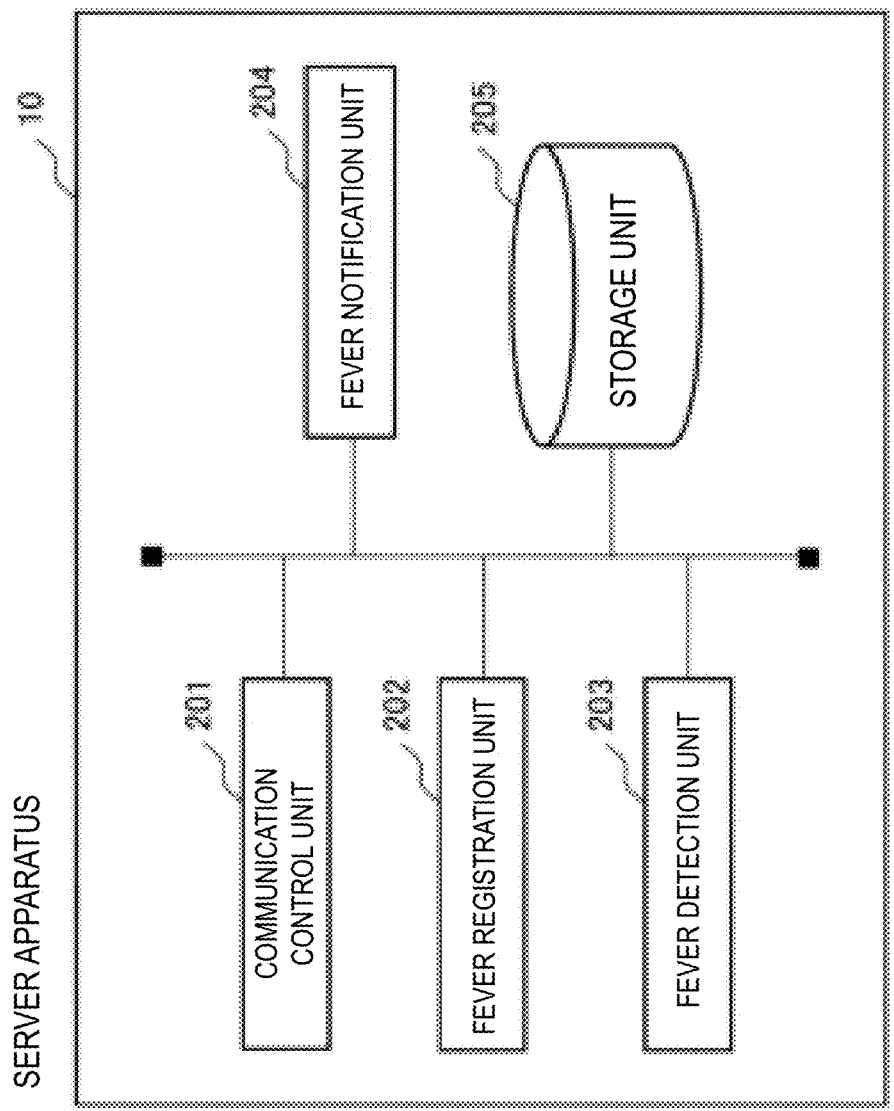
FIG. 3 is a diagram illustrating an example of a processing configuration of a server apparatus according to the first example embodiment.

FIG. 3 is a diagram for illustrating an example of a processing configuration (processing modules) of the server apparatus 10 according to the first example embodiment. Referring to FIG. 3, the server apparatus 10 includes a communication control unit 201, a fever registration unit 202, a fever detection unit 203, a fever notification unit 204 and a storage unit 205.

The communication control unit 201 is means for controlling communication with other devices. For example, the communication control unit 201 receives image data (packets including image data) from the first camera device 20 and the second camera device 30. The communication control unit 201 transmits data to the terminal 40.

The fever registration unit 202 is means for registering a person with fever in a system. The fever registration unit 202 acquires thermal image data and image data from the first camera device 20. The fever registration unit 202 determines whether or not a person (a first person) passing through a corridor (a first location) connecting a runway and an airport terminal is a person with fever based on the thermal image data. The fever registration unit 202 acquires biometric information of the person with fever from normal image data (first image data) and also registers the biometric information of the person with fever in a fever information database.

The fever registration unit 202 analyzes thermal image data to determine whether or not a photographed person in the image data has a fever. Specifically, the fever registration unit 202 counts a number of pixels whose value is higher than a first threshold value (e.g., 37.5 degrees Celsius) among a plurality of pixel values including the thermal image data. The fever registration unit 202 determines that a person in the thermal image data is the person with fever when the number of pixels whose temperature is higher than the above threshold value is greater than a second threshold value. The fever registration unit 202 determines that the person in the thermal image data is not the person with fever when the number of pixels whose temperature is higher than the above threshold value is less than a second threshold value. Thus, the fever registration unit 202 determines whether or not the subject (the photographed person) of thermal image data is the person with fever based on the number of pixels in thermal image data whose pixel values is equal to or greater than a predetermined value.

Alternatively, the fever registration unit 202 may use a pre-prepared learning model (an identification model) to determine whether or not the photographed person is the person with fever. More specifically, the fever registration unit 202 may determine whether or not the photographed person is the person with fever by inputting thermal image data into the learning model. For example, a learning model (an estimator) is prepared in advance that outputs a determination result as to whether or not the photographed person is the person with fever when thermal image data is input. The above learning model is acquired by preparing a large amount of thermal image data to which labels (a person with fever and a person with non-fever) are assigned and learning the data using the data as teacher data. Any algorithm, such as support vector machine, boosting, or neural network, may be used to generate the learning model. Since known techniques can be used for the above algorithms such as support vector machine, description thereof will be omitted.

When the photographed person is not the person with fever, the fever registration unit 202 does not perform any particular processing. The fever registration unit 202 discards image data (thermal image data and image data) acquired from the first camera device 20.

When the photographed person is the person with fever, the fever registration unit 202 calculates a body surface temperature of the person with fever. For example, the fever registration unit 202 calculates an average value of temperature of pixels whose temperature is higher than a first threshold value (e.g., 37.5 degree Celsius) as a body surface temperature of the person with fever.

Also, when the photographed person is the person with fever, the fever registration unit 202 attempts to extract a face image from image data acquired from the first camera device 20.

When no face image can be extracted, the fever registration unit 202 discards image data (thermal image data and image data) acquired from the first camera device 20. When a face image can be extracted, the fever registration unit 202 generates feature values (a feature vector consisting of multiple feature values) from the face image.

An existing technique can be used for an extraction process of a face image and a generation process of a feature value performed by the fever registration unit 202, and therefore, detailed description thereof will be omitted. For example, the fever registration unit 202 may extract a face image (a face area) from the image data by using a learning model learned by a CNN (Convolutional Neural Network). Alternatively, the fever registration unit 202 may extract a face image by using a technique such as template matching.

In addition, with respect to generation of feature value, the fever registration unit 202 extracts eyes, a nose, a mouth, and so on from a face image, as the feature points. Next, the fever registration unit 202 calculates the location of an individual feature point and the distance between feature points as feature values and generates a feature vector formed by the plurality of feature values (vector information that characterizes the face image).

The fever registration unit 202 stores the generated feature value, the face image of a person with fever (the extracted face image), and the body surface temperature, and so on in the fever information database in correspondence. FIG. 4 is a diagram illustrating an example of the fever information database according to the first example embodiment.

Referring to FIG. 4, the fever information database stores a fever ID, biometric information (a face image and a feature value) of a person with fever and a body surface temperature in correspondence. The fever ID is an identifier to uniquely identify a person with fever and is numbered each time an entry is added to the fever information database.

The fever detection unit 203 is means for detecting a person with fever in an airport. The fever detection unit 203 acquires image data from the second camera device 30. The fever detection unit 203 uses biometric information of a person (a second person) in image data (second image data) acquired from the second camera device 30 and biometric information registered in the fever information database to detect a person with fever located at a second location (an airport terminal).

Specifically, the fever detection unit 203 attempts to extract a face image from image data. When no face image can be extracted, the fever detection unit 203 does not perform any particular operation. In this case, the fever detection unit 203 discards image data acquired from the second camera device 30.

When a face image can be extracted, the fever detection unit 203 generates feature value from the extracted face image. The fever detection unit 203 performs matching processing by using the generated feature value and the feature values registered in the fever information database.

The fever detection unit 203 performs 1-to-N matching by setting the above generated feature value on a matching side and the feature values registered in the fever information database on a registration side, respectively. The fever detection unit 203 calculates a similarity between feature value on the matching side and each of the multiple feature values on the registration side. For the individual similarity, the chi-squared distance, the Euclidean distance, or the like may be used. A large distance represents a lower similarity, and a smaller distance represents a higher similarity.

The fever detection unit 203 determines that the matching is successful when there is a feature value whose similarity between the feature value and the feature value to be matched exceeds a predetermined value among a plurality of feature values registered in the fever information database.

When matching fails, the fever detection unit 203 does not perform any particular operation.

When the matching is successful, the matching unit 203 hands a fever ID in the fever information database identified by the matching processing over to the fever notification unit 204.

When multiple face images are extracted from image data acquired from the second camera device 30, the matching unit 203 may perform a matching processing for each face image to determine whether or not each photographed person is a person with fever.

The fever notification unit 204 is means for notifying a staff member in an airport of a presence of a person with fever. The fever notification unit 204 transmits a fever detection notification, including a detected biometric information of the person with fever, to the terminal 40 for the staff member to guide the person with fever to an inspection room (a third location).

The fever notification unit 204 reads out a face image corresponding to the fever ID acquired from the fever detection unit 203 from the fever information database. The fever notification unit 204 transmits the fever detection notification including a readout face image to the terminal 40 owned by the staff member.

Figure 5:
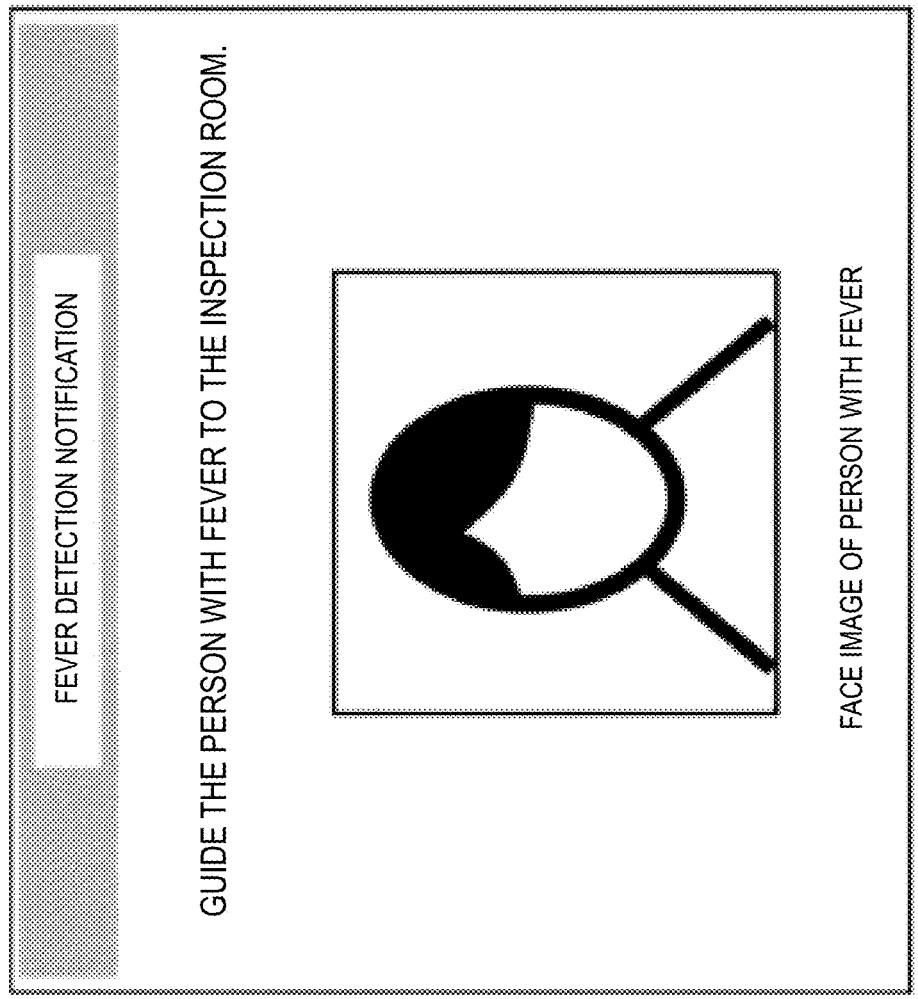
FIG. 5 is a diagram illustrating an operation of a fever notification unit according to the first example embodiment.

Upon receipt of the notification, terminal 40 displays a message as shown in FIG. 5. The staff member who sees the display shown in FIG. 5 look for a person with fever in the vicinity where the second camera device 30 is installed. The staff member guides the person with fever whom he/she located to an inspection room.

The storage unit 205 is means for storing information necessary for an operation of the server apparatus 10.

[Other Devices]

A detailed description of a processing configuration and so on for the first camera device 20, the second camera device 30, and the terminal 40 is omitted. This is because it is possible to use existing devices as these devices and it is obvious to those skilled in the art. For example, the terminal 40 is a cell phone or smartphone. A processing configuration of the gate apparatus 50 will be discussed below.

[Operation of Server Apparatus]

Next, an operation of the server apparatus 10 according to the first example embodiment will be described.

Figure 6:
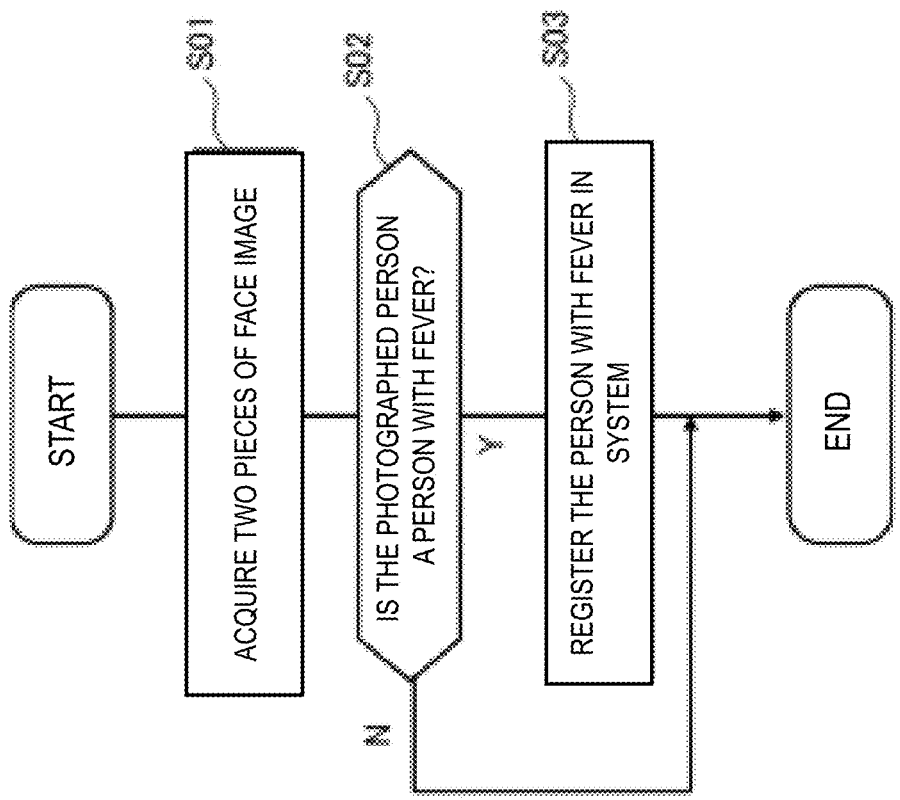
FIG. 6 is a flowchart illustrating an example of an operation of a server apparatus according to the first example embodiment.

FIG. 6 is a flowchart illustrating an example of an operation of the server apparatus 10 according to the first example embodiment. Referring to FIG. 6, the operation of the server apparatus 10 when registering a person with fever to the system is described.

The server apparatus 10 acquires two pieces of image data (thermal image data and normal image data) from the first camera device 20 (step S01).

The server apparatus 10 analyzes the thermal image data to determine whether or not a photographed person is a person with fever (step S02). When the photographed person is not the person with fever (step S02, No branch), the server apparatus 10 does not perform any particular operation.

When the photographed person is the person with fever (step S02, Yes branch), the server apparatus 10 generates feature value from the normal image data and registers information of the person with fever including the feature value in the system (step S03). The server apparatus 10 stores biometric information of the person with fever in the fever information database.

Figure 7:
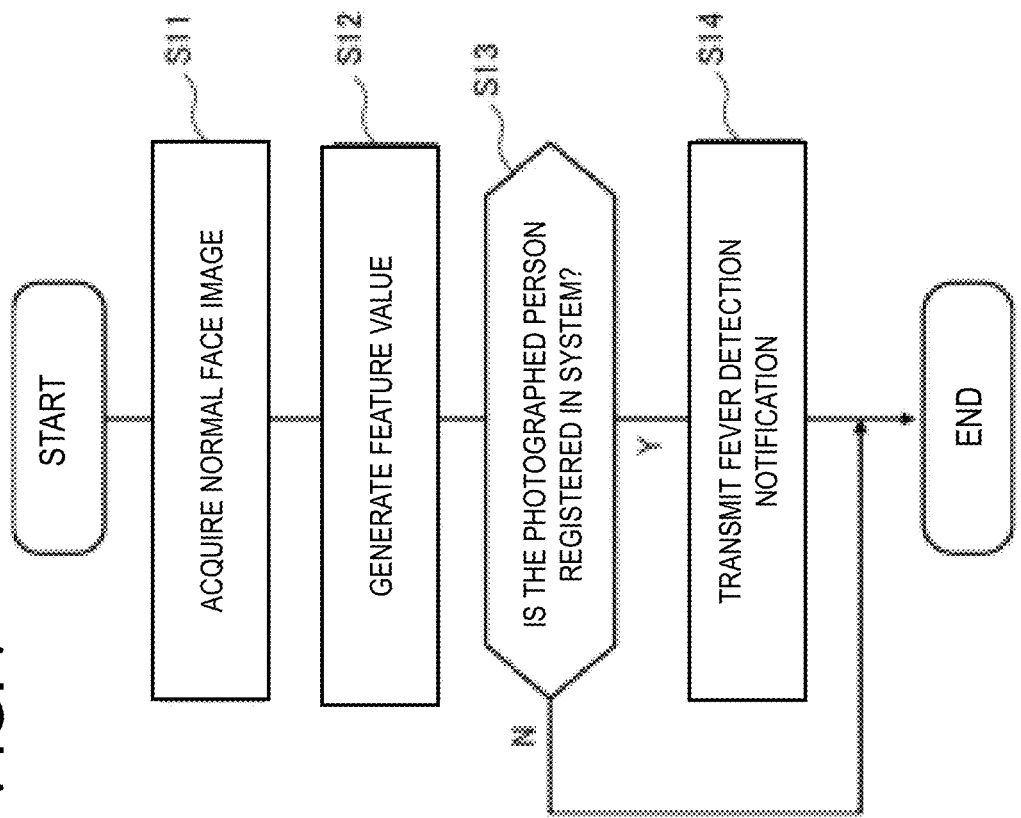
FIG. 7 is a flowchart illustrating an example of an operation of a server apparatus according to the first example embodiment.

FIG. 7 is a flowchart illustrating an example of an operation of the server apparatus 10 according to the first example embodiment. Referring to FIG. 7, the operation of the server apparatus 10 when instructing a staff member to guide (isolate in an inspection room) a person with fever to an inspection room is described.

The server apparatus 10 acquires normal image data from the second camera device 30 (step S11).

The server apparatus 10 extracts face image from the normal image data and generates feature value (step S12).

The server apparatus 10 determines whether a photographed person included in the normal image data is registered in the system (step S13). The server apparatus 10 performs matching processing by using generated feature value and feature values stored in the fever information database to determine whether or not the photographed person is registered as a person with fever.

When the photographed person is not the person with fever (step S13, No branch), the server apparatus 10 does not perform any particular processing.

When the photographed person is the person with fever (step S13, Yes branch), the server apparatus 10 transmits a fever detection notification to the terminal 40 owned by a staff member (step S14). The staff member who sees information regarding the person with fever displayed on the terminal 40 goes to the person with fever and guides the person with fever to the inspection room.

As described above, the server apparatus 10 of the first example embodiment acquires image data including a face image of a passenger and thermal image data including a body surface temperature. The server apparatus 10 registers biometric information of a person with fever whose body surface temperature is greater than a predetermined value with the system. The server apparatus 10 acquires image data from the second camera device 30 installed at a location different from that of the first camera device 20. The server apparatus 10 determines whether or not a photographed person in image data is a person with fever registered in the system. The server apparatus 10 transmits a fever detection notification including biometric information (a face image) of the person with fever photographed by the second camera device 30 to the terminal 40 owned by the staff member. The staff member goes to the person with fever by relying on the face image of the person with fever (the unwell person) displayed on the terminal 40. The staff member guides the person with fever to an inspection room. As a result, the staff member can easily locate the person with fever and the inspection of the person with fever can be reliably performed.

Second Example Embodiment

Next, a second example embodiment will be described in detail with reference to drawings.

The first example embodiment describes a case in which staff member in an airport guide a person with fever registered in the system to an inspection room.

The second example embodiment describes a case in which the server apparatus 10 guides a person with fever to an inspection room.

As a configuration of a fever guide system according to the second example embodiment can have the same configuration as that according to the first example embodiment, the description thereof will be omitted.

The following description will be made with a focus on a difference between the first and second example embodiments.

A camera device 30 according to the second example embodiment includes two lenses. The second camera device 30 is a so-called stereo camera and is capable of photographing a subject from different directions. By using a plurality of image data acquired from the second camera device 30, a distance in the depth direction can be measured.

Figure 8:
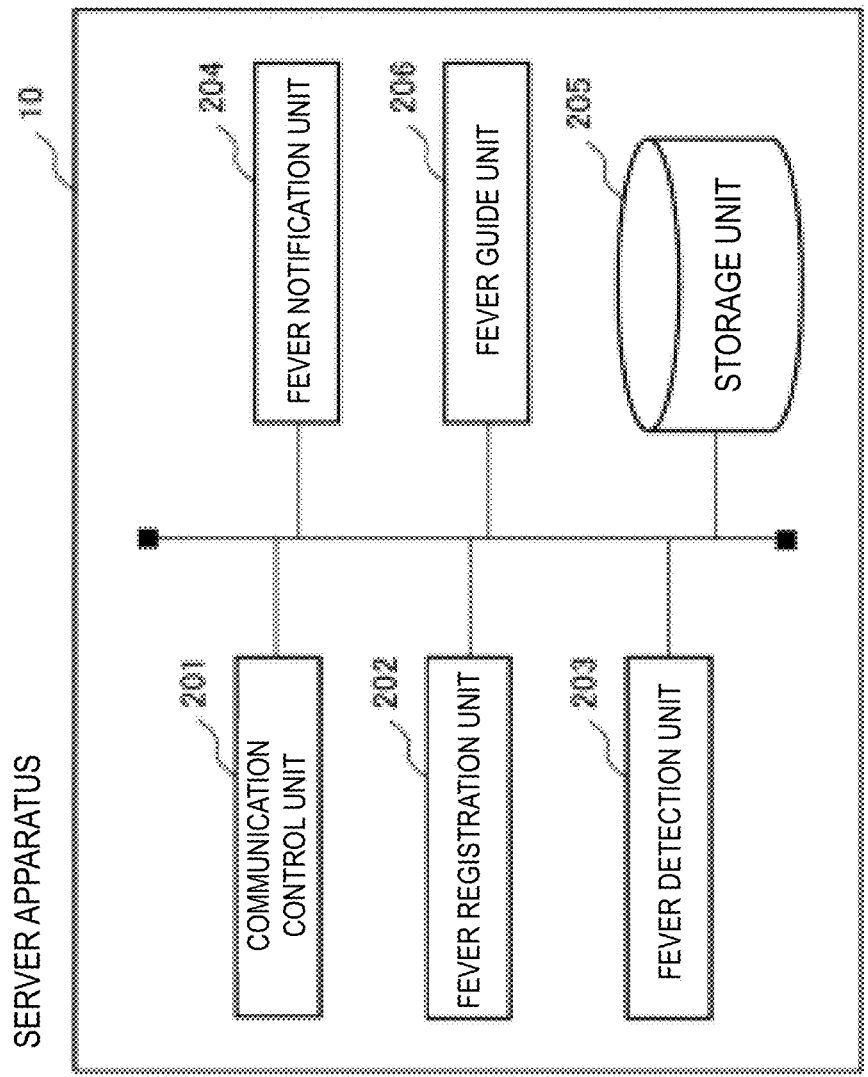
FIG. 8 is a diagram illustrating an example of a processing configuration of a server apparatus according to a second example embodiment.

FIG. 8 is a diagram for illustrating an example of a processing configuration (processing modules) of the server apparatus 10 according to the second example embodiment. Referring to FIG. 8, a fever guide unit 206 is added to the configuration for the first example embodiment.

The server apparatus 10 according to the second example embodiment may or may not include a fever notification unit 204. That is, the server apparatus 10 may urge the person with fever to move to an inspection room while notifying a staff member of a presence of a person with fever, or it may not notify the staff member of the presence of the person with fever.

When the fever detection unit 203 of the second example embodiment detects a person with fever, the fever detection unit 203 hands over a fever ID of the person with fever and normal image data (two pieces of normal image data with different shooting directions) acquired from the second camera device 30 to the fever guide unit 206.

The fever guide unit 206 is means for guiding a person with fever at a second location (a person with fever photographed by the second camera device 30) to an inspection room. The fever guide unit 206 analyzes normal image data acquired from a fever notification unit 204 to calculate a location of the person with fever (XY coordinates in an absolute coordinate system with one point in an airport terminal as an origin).

The fever guide unit 206 extracts a face image from one of the two pieces of image data. The fever guide unit 206 stores a position at which the face image is extracted (the position in the image coordinate system).

Next, the fever guide unit 206 calculates a distance from the second camera device 30 to a subject (a person with fever) using a parallax between the two pieces of image data. The fever guide unit 206 calculates a position of the person with fever using the previously stored position where the face image is detected and a distance between the second camera device 30 and the person with fever.

Note that detailed explanations are omitted since existing techniques can be used to calculate the distance between the camera and the subject using parallax and a process of calculating a position in an absolute coordinate system.

The fever guide unit 206 outputs a message in a vicinity of the person with fever whose location has been identified. For example, the fever guide unit 206 outputs a message in the vicinity of the person with fever (at the feet of the person with fever) using a projection device such as a projector. Specifically, the fever guide unit 206 outputs a message that suggests that the person with fever move to the inspection room.

Figure 9A:
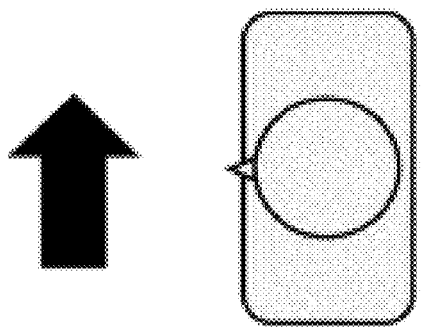
FIG. 9 is a diagram illustrating an operation of a fever guide unit according to the first example embodiment.
Figure 9B:
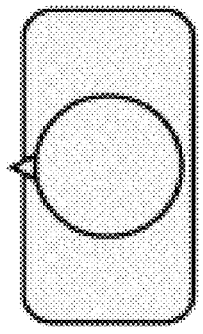

For example, the fever guide unit 206 may output a message as shown in FIG. 9(a), or the fever guide unit 206 may output an indication (as shown in FIG. 9(b)) that enables the person with fever to grasp a traveling direction easily intuitively. Alternatively, the fever guide unit 206 may output a message at the feet of the person with fever, such as "You must have an inspection before immigration examination." Alternatively, the fever guide unit 206 may output a message (an inspection required before immigration examination) at the feet of a passenger passing through a corridor between a runway and an airport terminal in order to inform a passenger that an inspection is required for a person with fever. That is, the fever guide unit 206 may output messages not only to the second location (wide location) where the second camera device 30 is installed, but also to the first location (narrow corridor) where the first camera device is installed.

A liquid crystal monitor may be embedded in a floor near the second camera device 30, and the fever guide unit 206 may use the liquid crystal monitor to output the message shown in FIG. 9. Alternatively, the fever guide unit 206 may output an audio message toward a current location of the person with fever by using a highly directional speaker (a parametric speaker).

Further the second example embodiment describes a case in which a stereo camera is used as the second camera device 30 to accurately calculate a position of a person with fever.

However, since the second camera device 30 is fixedly installed on a ceiling and so on an approximate location of a photographed person can be grasped in advance. Therefore, when a person with fever is detected, the server apparatus 10 may output a message to a location predetermined from a location of the second camera device 30 or elsewhere.

As described above, the server apparatus 10 according to the second example embodiment guides a person with fever to an inspection room. More specifically, the server apparatus 10 identifies a location of the person with fever detected by the second camera device 30 based on two pieces of image data with different shooting directions, and displays a message at an identified location to direct the person with fever to an inspection room. As a result, it is possible to inspect a person with fever even when there are no staff members present at an airport.

Third Example Embodiment

Next, a third example embodiment will be described in detail with reference to the drawings.

The first and second example embodiments describe a case in which the fever guide system guides a person with fever to an inspection room. However, it is supposed that some persons with fever ignore guidance (instructions) from staff members and the server apparatus 10 and proceed to immigration examination procedures. Alternatively, when the number of persons with fever is large compared to the number of staff members stationed at an airport, it is assumed that staff members are unable to guide persons with fever to the inspection room.

In the third example embodiment, it will be described when a person with fever is prevented from moving out of an immigration examination area.

As a configuration of a fever guide system according to the third example embodiment can have the same configuration as that according to the first example embodiment, the description thereof will be omitted. In addition, as a processing configuration of the server apparatus 10 according to the third example embodiment can have the same processing configurations as those according to the first and second example embodiments, description thereof will be omitted.

The following description will be made with a focus on differences between the first to third example embodiments.

A gate apparatus 50 is an apparatus that examines whether or not a user is permitted to pass through a gate. More specifically, the gate apparatus 50 is an apparatus that carries out immigration examination of users.

The fever registration unit 202 of the server apparatus 10 in the third example embodiment transmits registered biometric information of a person with fever to the gate apparatus 50 when the person with fever is registered in a system. More specifically, the fever registration unit 202 transmits at least feature value of the person with fever (feature value generated from a face image) to the gate apparatus 50. For example, the fever registration unit 202 transmits feature value of the person with fever to the gate apparatus 50 each time a new entry is added to a fever information database.

Figure 10:
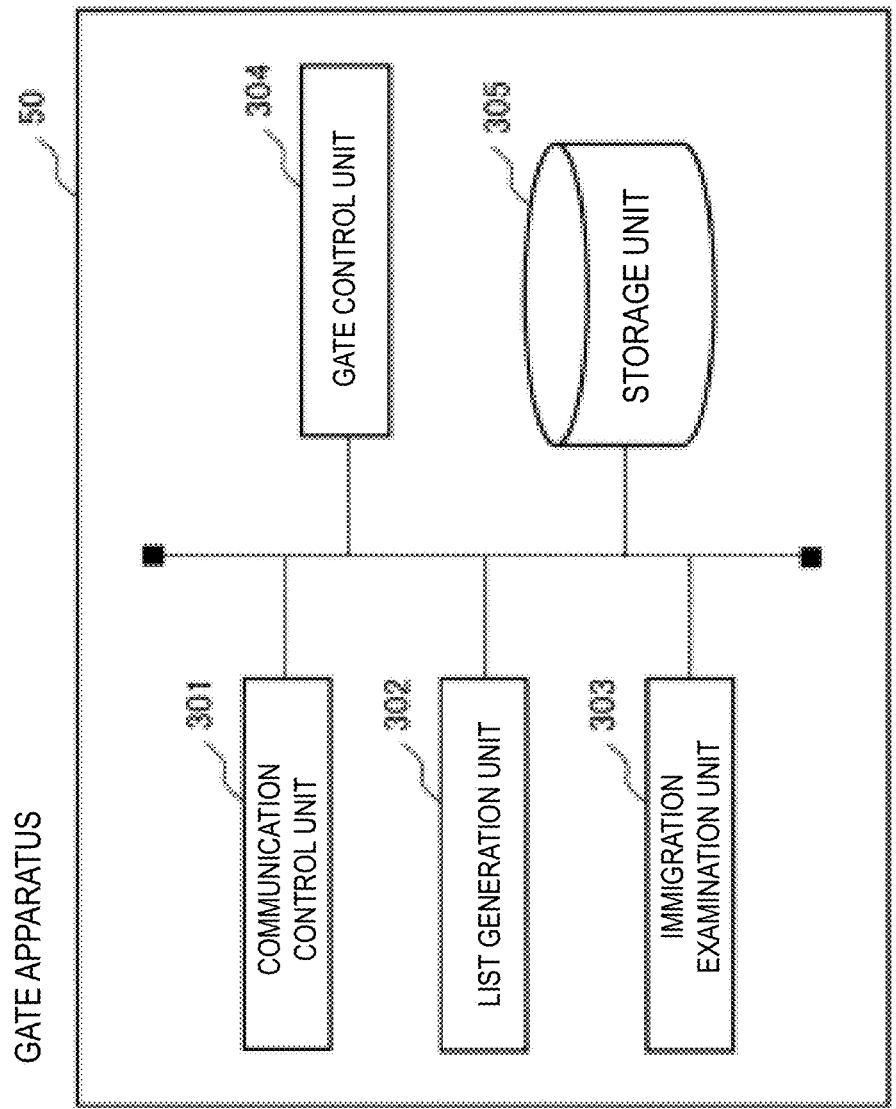
FIG. 10 is a diagram illustrating an example of a processing configuration of a gate apparatus according to a third example embodiment.

FIG. 10 is a diagram illustrating an example of a processing configuration (processing modules) of the gate apparatus 50 according to the third example embodiment. As illustrated in FIG. 10, the gate apparatus 50 includes a communication control unit 301, a list generation unit 302, an immigration examination unit 303, a gate control unit 304, a gate control unit 304, and a storage unit 305.

The communication control unit 301 is means for controlling communication with other devices. Specifically, the communication control unit 301 receives data (packets) from the server apparatus 10. In addition, the communication control unit 301 transmits data to the server apparatus 10.

The list generation unit 302 is means for generating a "fever list" using feature value of a person with fever received from the server apparatus 10. The list generation unit 302 manages feature value acquired from the server apparatus 10 as a list (see FIG. 11).

The immigration examination unit 303 is means for immigration examination of a passenger. The immigration examination unit 303 permits a person to be examined to enter a country when the person is not a person with fever and possesses a valid passport.

The immigration examination unit 303 controls a camera device installed in its own device and acquires face image of the person to be examined. The immigration examination unit 303 generates feature value from the face image.

The immigration examination unit 303 determines whether or not the person to be examined is on the fever list. Specifically, the immigration examination unit 303 performs 1-to-N matching by setting the above generated feature value of the person to be examined to a matching side and the feature values listed on the fever list to a registration side, respectively.

When the matching is successful (when the person to be examined is on the fever list), the immigration examination unit 303 sets a result of examination of the person to be examined to "immigration denial".

When the matching fails (i.e., the person to be examined is not on the fever list), the immigration examination unit 303 determines whether or not the person to be examined possesses a valid passport. Specifically, the immigration examination unit 303 acquires a face image (feature value) stored in an IC (Integrated Circuit) chip of the passport possessed by the person to be examined. The immigration examination unit 303 determines whether or not the face image acquired from the IC chip in the passport and the face image of the person to be examined (the face image photographed by the gate apparatus 50) are those of the same person. More specifically, the immigration examination unit 303 performs a one-to-one matching by using two face images (feature values generated from the face images).

When the one-to-one matching fails (i.e., the face image in the passport and the face image of the person to be examined are those of a different person), the immigration examination unit 303 sets the result of the examination of the person to be examined to "immigration denial".

When the one-to-one matching is successful (i.e., the face image in the passport and the face image of the person to be examined are of the same person), the immigration examination unit 303 sets the result of the examination of the person to be examined to "immigration permission".

The immigration examination unit 303 notifies the gate control unit 304 of the result of the examination (immigration permission or immigration denial).

The gate control unit 304 is means for controlling a gate provided by the gate apparatus 50. The gate control unit 304 opens the gate and permits the person to be examined to pass through the gate when the result of the examination is immigration permission. The gate control unit 304 does not permit the person to be examined to pass through the gate when the result of the examination is immigration denial.

The storage unit 305 is means for storing information necessary for an operation of the gate apparatus 50.

[Operation of Gate Apparatus]

Next, an operation of the gate apparatus 50 according to the third example embodiment will be described.

Figure 12:
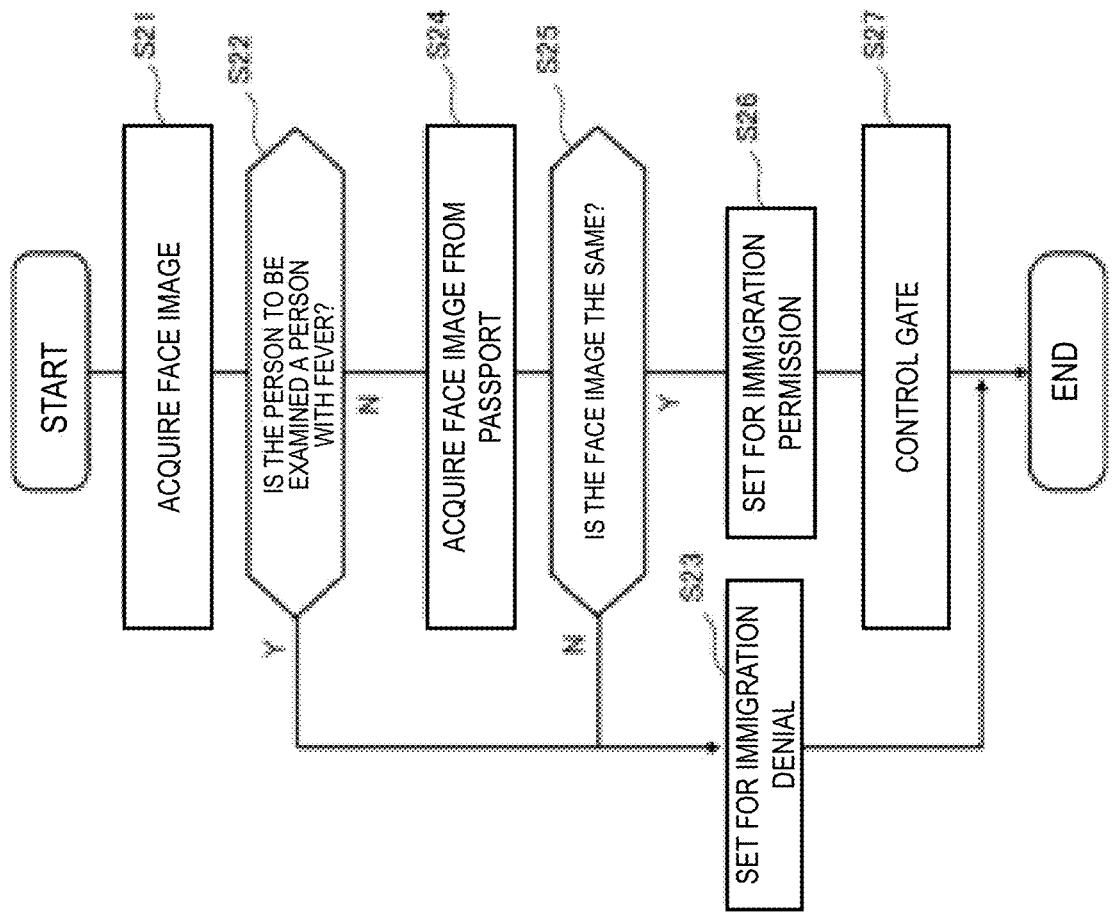
FIG. 12 is a flowchart illustrating an example of an operation of a gate apparatus according to the third example embodiment.

FIG. 12 is a flowchart illustrating an example of the operation of the gate apparatus 50 according to the third example embodiment. The description of the operation of acquiring feature value of a person with fever and generating a fever list of persons with fever is omitted.

The gate apparatus 50 acquires biometric information (a face image) of a person to be examined (step S21).

The gate apparatus 50 determines whether or not the person to be examined is a person with fever (step S22). The gate apparatus 50 performs the above determination by a matching processing using feature value generated from the face image of the person to be examined and the feature value registered in the fever list.

When the person to be examined is the person with fever (step S22, Yes branch), the gate apparatus 50 sets the result of the examination to "immigration denial" (step S23).

When the person to be examined is not the person with fever (step S22, No branch), the gate apparatus 50 acquires biometric information (a face image) from the passport possessed by the person to be examined (step S24).

The gate apparatus 50 determines whether or not the face image of the person to be examined and the face image stored in the passport are substantially same (step S25). Specifically, the gate apparatus 50 performs the above determination by the matching processing using the two pieces of biometric information.

When the two face images are not substantially same (step S25, No branch), the gate apparatus 50 sets the result of the immigration examination to "immigration denial" (step S23).

When the two face images are substantially same (step S25, Yes branch), the gate apparatus 50 sets the result of the immigration examination to "immigration permission" (step S26).

The gate apparatus 50 controls the gate according to the result of the examination (step S27).

As described above, in the fever guide system according to the third example embodiment, the gate apparatus 50 determines whether or not a person to be examined is a person with fever using biometric information of the person with fever transmitted from the server apparatus 10. The gate apparatus 50 denies the person to be examined to pass through the gate when the person to be examined is the person with fever. As a result, it is possible to prevent the person with fever (an unwell person) from entering a country beyond an immigration examination area. In addition, even when the gate apparatus 50 does not have a thermal camera (an infrared camera), but only a regular camera, the gate apparatus is able to detect the person with fever and prevent the person with fever from entering a country.

Figure 13:
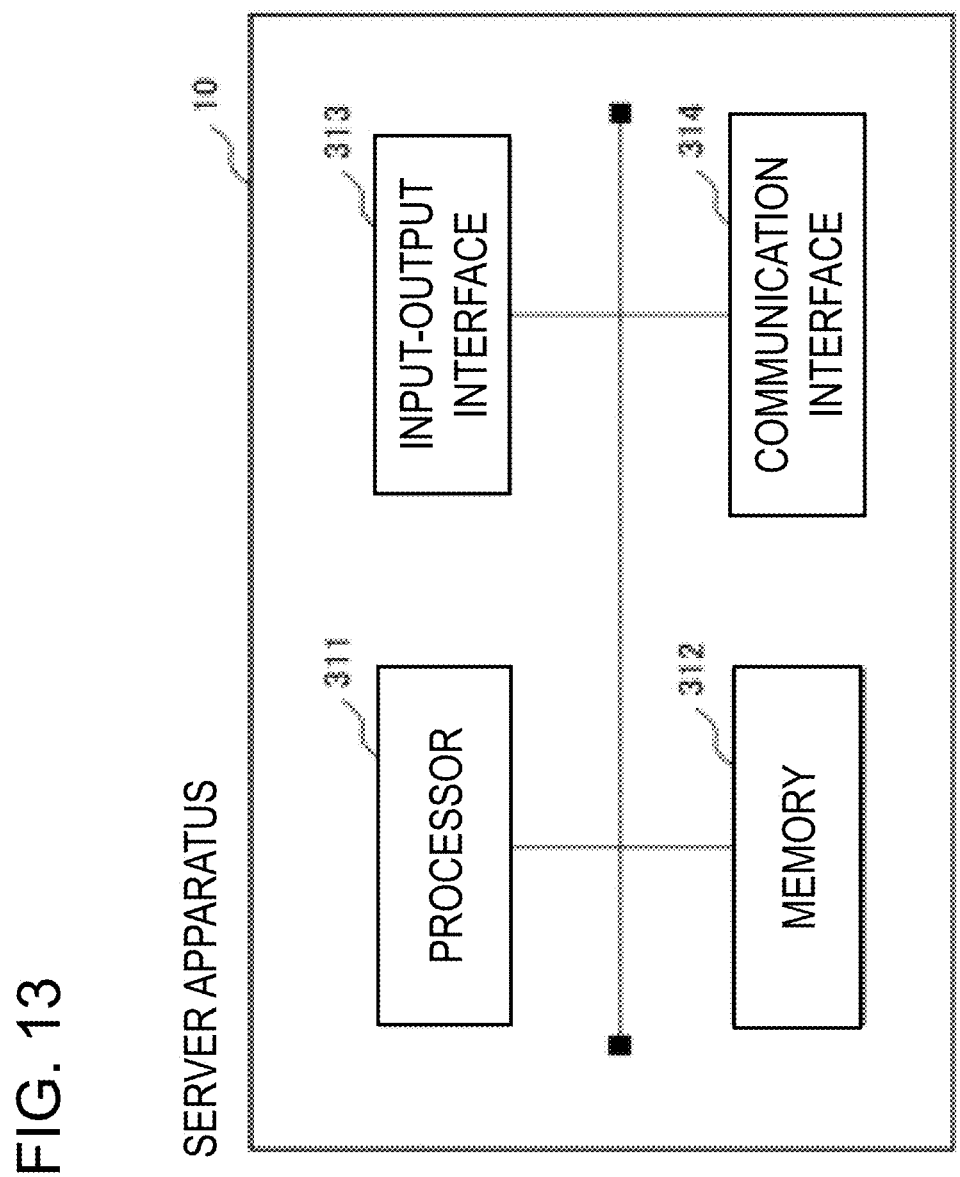
FIG. 13 is a diagram illustrating an example of a hardware configuration of the server apparatus of the present application.

Next, a hardware configuration of an individual apparatus that constitutes the fever guide system will be described. FIG. 13 is a diagram illustrating an example of a hardware configuration of the server apparatus 10.

The server apparatus 10 can be configured by an information processing apparatus (a so-called computer) and has a configuration illustrated as an example in FIG. 13. For example, the server apparatus 10 includes a processor 311, a memory 312, an input-output interface 313, a communication interface 314, and so on. The components such as the above processor 311 are connected to an internal bus and so on so that the components can mutually communicate with each other.

The hardware configuration of the server apparatus 10 is not limited to the configuration illustrated in FIG. 13. The server apparatus 10 may include hardware not illustrated or may be configured without the input-output interface 313 if desired. In addition, the number of components, such as the number of processors 311, included in the server apparatus 10 is not limited to the example illustrated in FIG. 13. For example, a plurality of processors 311 may be included in the server apparatus 10.

For example, the processor 311 is a programmable device such as a CPU (Central Processing Unit), an MPU (Micro Processing Unit), or a DSP (Digital Signal Processor). Alternatively, the processor 311 may be a device such as an FPGA (Field Programmable Gate Array) or an ASIC (Application Specific Integrated Circuit). The processor 311 executes various kinds of programs including an operating system (OS).

The memory 312 is a RAM (Random Access Memory), a ROM (Read-Only Memory), an HDD (Hard Disk Drive), an SSD (Solid State Drive), or the like. The memory 312 stores an OS program, an application program, and various kinds of data.

The input-output interface 313 is an interface for a display apparatus and an input apparatus not illustrated. For example, the display apparatus is a liquid crystal display or the like. For example, the input apparatus is an apparatus that receives user operations, and examples of the input apparatus include a keyboard and a mouse.

The communication interface 314 is a circuit, a module, or the like for performing communication with other apparatuses. For example, the communication interface 314 includes a NIC (Network Interface Card) or the like.

The function of the server apparatus 10 is realized by various kinds of processing modules. The processing modules are realized, for example, by causing the processor 311 to execute a program stored in the memory 312. In addition, this program can be recorded in a computer-readable storage medium. The storage medium may be a non-transient (non-transitory) storage medium, such as a semiconductor memory, a hard disk, a magnetic recording medium, or an optical recording medium. That is, the present invention can be embodied as a computer program product. In addition, the above program may be updated by downloading a program via a network or by using a storage medium in which a program is stored. In addition, the above processing modules may be realized by semiconductor chips.

The descriptions of the hardware configurations of the first camera device 20, the second camera device 30 and the terminal 40 are omitted. This is because these hardware configurations are obvious to those skilled in the art. The description of the hardware configuration regarding the gate apparatus 50 is also omitted. The gate apparatus 50 may include a processor, a memory, and so on like the server apparatus 10 and may include a camera device for photographing a person to be examined and a card reader for acquiring information from a passport.

The server apparatus 10 includes a computer and can realize its functions by causing the computer to execute a program. In addition, the server apparatus 10 executes a control method of the server apparatus by using this program.

[Variation]

Here, the configurations, operations, and so on of the fever guide system according to the above example embodiments are examples and do not limit the present system configuration and so on.

The above example embodiments describe a case in which the server apparatus 10 include a fever information database. However, the fever information database constructed on the server apparatus 10 may be constructed on a database server different from the server apparatus 10. The fever guide system may include the various means (e.g., fever registration unit 202 and so on) described in the above example embodiments.

The above example embodiments describe a case in which an unwell person is detected based on a body surface temperature of a photographed person, but an unwell person may be detected based on other indicators.

The above example embodiments describe a case in which a face image or feature value generated from the face image is used as biometric information for registering a person with fever in the system or for detecting the person with fever. However, it is not intended to limit biometric information that can be used in the present application to a face image or feature value generated from the face image. For example, biometric information such as an iris image, a finger vein image, a palm print image, a palm vein image, and so on may be used.

The server apparatus 10 may delete information of a person with fever (an entry in the fever information database) after a predetermined period of time has passed. Alternatively, the server apparatus 10 may delete an entry for the person with fever who has moved to an inspection room. In this case, for example, the server apparatus 10 receives a "fever guide completion notification" from the terminal 40 owned by a staff member. The server apparatus 10 deletes an entry in the fever information database upon receiving the notification. For example, when the staff member completes to guide the person with fever to the inspection room according to the fever detection notification shown in FIG. 5, the staff member operates the terminal 40 and transmits the fever guidance completion notification. At that time, the terminal 40 includes a face image acquired from the server apparatus 10 in the above notification, so that the server apparatus 10 is able to identify the person with fever (the entry of the person with fever) for whom the guidance is completed. Alternatively, by transmitting and receiving a fever ID between the server apparatus 10 and terminal 40, the person with fever to be guided and the person with fever for whom the guidance is completed may be identified.

In the above example embodiments, it is described that the fever detection is performed when a passenger enters a country. However, the fever detection may be performed when the passenger leaves the country. The fever detection may also be performed at facilities other than airports, such as ports, train stations, and event venues (e.g., baseball stadiums, soccer stadiums, concert halls).

Figure 14:
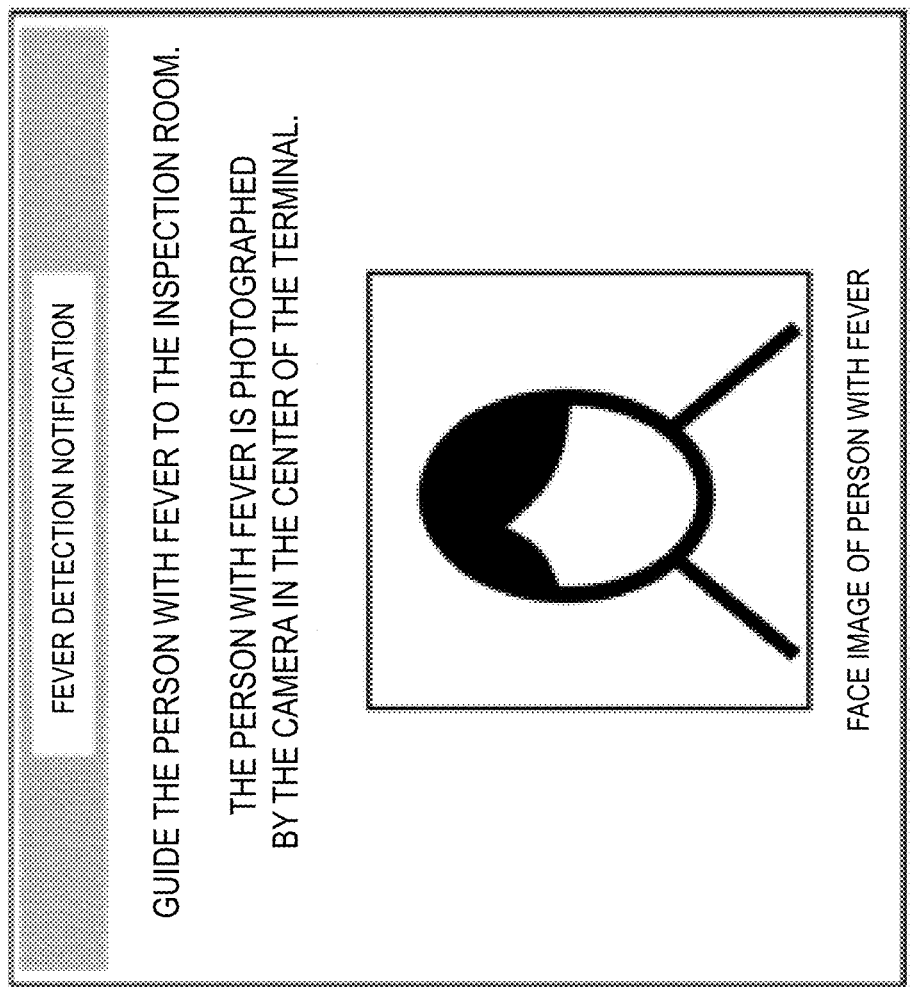
FIG. 14 is a diagram illustrating an operation of a terminal according to a variation of the present application.

The above example embodiments describe a case when a single second camera device 30 is installed in the system. Here, when a plurality of second camera devices 30 are installed, each of the second camera devices 30 may transmit normal image data to the server apparatus 10 along with a camera ID to identify its own device. The server apparatus 10 may identify the second camera device 30 that photographed a person with fever based on the camera ID. In this case, the server apparatus 10 may transmit a fever detection notification including a location (an installation location) of the second camera device 30 to the terminal 40. The terminal 40 may perform the display shown in FIG. 14 using the acquired fever detection notification.

The above example embodiments describe a case in which the server apparatus 10 determines whether or not the photographed person is a person with fever by using thermal image data and generates feature value for the person with fever. However, the server apparatus 10 may extract a face image from image data first and then determine whether or not the person in an extracted face image is a person with fever. It is possible to reverse an order of a fever determination and a face image extraction process in this way. Further by extracting a face image first, the server apparatus 10 is able to easily narrow down an area for a fever detection. Specifically, the server apparatus 10 is able to determine whether or not a photographed person is a person with fever by performing a threshold processing on pixel value of thermal image data corresponding to an area from which a face image of image data is extracted. These processes also enable the server apparatus 10 to determine whether or not each photographed person is the person with fever, even when image data and thermal image data include two or more photographed persons.

The third example embodiment describes a case when the server apparatus 10 transmits information of a person with fever to the gate apparatus 50. However, the gate apparatus 50 may transmit biometric information (a face image and feature value) of a person to be examined to the server apparatus 10. In this case, the server apparatus 10 may determine whether the person to be examined is the person with fever by using the fever information database. The server apparatus 10 notifies the gate apparatus 50 of a determination result, and the gate apparatus 50 may control a gate based on the determination result.

When the server apparatus 10 is unable to acquire sufficient feature value for a matching processing from a face image of image data acquired from the first camera device 20, the server apparatus 10 may store a body shape and clothing of a photographed person as feature of the photographed person. For example, when the photographed person is wearing a mask, sunglasses, and so on it is assumed that sufficient feature value cannot be acquired for a matching processing. In this case, the server apparatus 10 may register feature value such as a body shape of the photographed person in the system. Further in this case, the server apparatus 10 may transmit image data that include the body shape and clothing of the photographed person to the terminal 40. A staff member who sees such image data may ask the photographed person to remove his/her mask, sunglasses, and so on and measure his/her body surface temperature. That is, a staff member may have an opportunity to determine whether or not a photographed person for whom feature value failed to be generated due to a mask or other reason is a person with fever again.

When a large number of second camera devices 30 is installed in the system, the server apparatus 10 may process image data acquired from the second camera devices 30 in a prioritized order. For example, the server apparatus 10 may prioritize a processing of image data acquired from the second camera device 30, which is located farther away from an immigration examination area, over a processing of image data acquired from the second camera device 30, which is located closer to the immigration examination area. This is because it is desirable for a staff member to catch a person with fever at a distance from the immigration examination area and guide (isolate) the person with fever to an inspection room.

Figure 15:
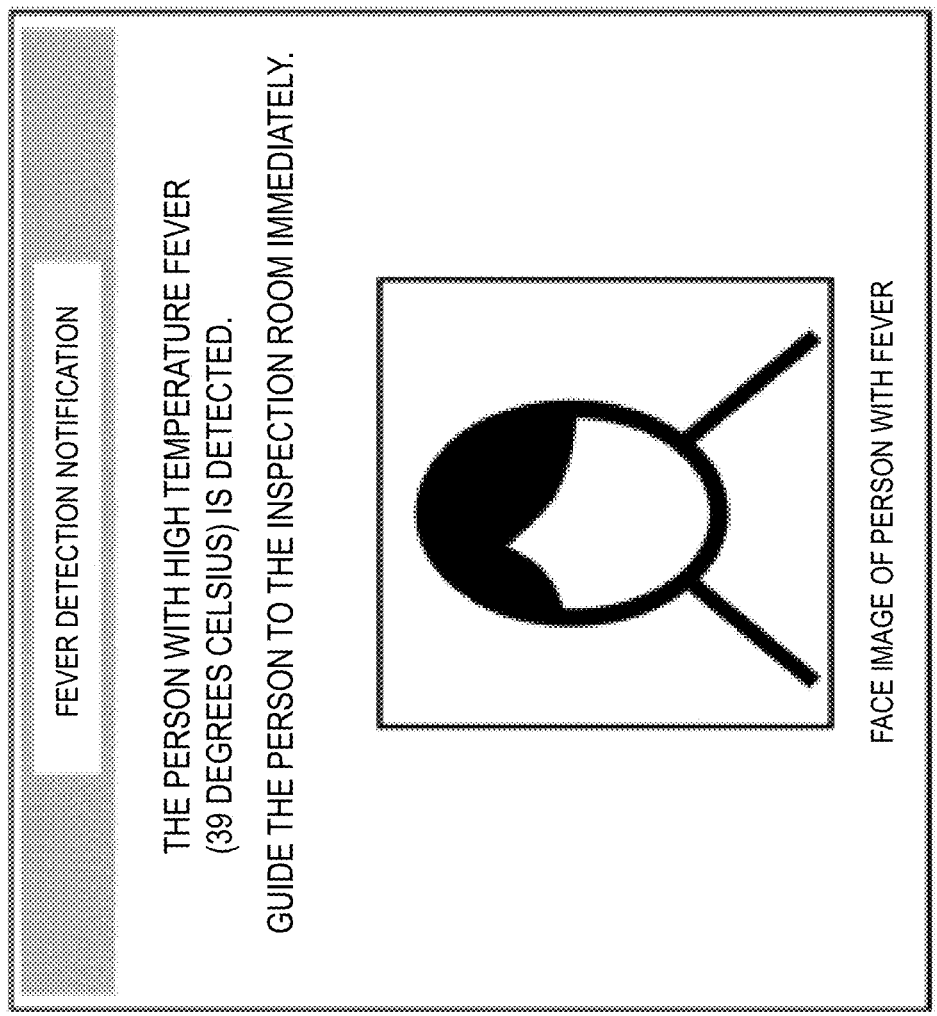
FIG. 15 is a diagram illustrating an operation of a terminal according to a variation of the present application.

The server apparatus 10 may transmit a fever detection notification including a body surface temperature of a person with fever to the terminal 40. In this case, the terminal 40 may change a content of the display according to the body surface temperature of the person with fever. For example, the terminal 40 may display an indication regarding the person with fever whose body surface temperature is extremely high (e.g., 39 degrees Celsius or higher), as well as an indication to instruct a staff member to quickly isolate the person with fever. In this case, for example, the terminal 40 may display as shown in FIG. 15, including the body surface temperature.

In the third example embodiment, when a person to be examined is denied passage through a gate, the gate apparatus 50 may notify the person to be examined of the reason why the person to be examined cannot pass through the gate. For example, the gate apparatus 50 may output the reason why the person cannot pass through the gate using a device such as a liquid crystal monitor or a speaker. For example, the gate apparatus 50 outputs that the person to be examined has a fever and cannot pass through the gate, or that the person cannot pass through the gate because he/she does not possess a valid passport. The gate apparatus 50 may also instruct a person with fever to head to an inspection room.

The server apparatus 10 may use the fever information database to manage whether or not a fever detection notification has been transmitted to a staff member with respect to a person with fever registered in the system. For example, as shown in FIG. 16, the above management may be performed by using a "detection status field" in the fever information database. When a person with fever is detected, the fever notification unit 204 checks the detection status field for the person with fever and does not transmit a fever detection notification for the person with fever when the field is set to "done". Alternatively, the fever notification unit 204 may determine whether or not to transmit a fever detection notification according to a body surface temperature of the person with fever and a setting value of the detection status field. For example, the fever notification unit 204 may transmit the fever detection notification to the terminal 40 with respect to a person with a high temperature fever, regardless of the setting value of the detection status field. This is because the person with a high temperature fever needs to be inspected without fail. That is, the server apparatus 10 may transmit the fever notification to the terminal 40 many times with respect to a passenger with the high degree of danger (urgency) (the person with high temperature fever).

In the above example embodiments, it is described that the server apparatus 10 transmits a fever detection notification to the terminal 40 owned by a staff member. Here, the fever detection notification may include a full body image of a person with fever as biometric information of the person with fever. In this case, the server apparatus 10 may register the full body image of the person with fever in the fever information database instead of or in addition to a face image extracted from image data when the person with fever is registered in the system. When the server apparatus 10 detects the person with fever from image data from the second camera device 30, the server apparatus 10 may transmit the fever detection notification including the full body image of the person with fever to the terminal 40. By displaying the full body image of the person with fever on the terminal 40, a staff member can locate the person with fever based on characteristics of his/her clothing. The staff member can easily locate a person with fever.

The server apparatus 10 may determine a period during which biometric information of a passenger is retained (a period during which biometric information is stored in the fever information database) based on various conditions. For example, the server apparatus 10 may determine a retention period according to a route of an aircraft coming down from a gate. The server apparatus 10 identifies a corridor through which a photographed person is passing according to an ID of the first camera device 20 (an ID such as IP address). The server apparatus 10 identifies an aircraft that landed at the gate connected to an identified corridor. The server apparatus 10 identifies the above aircraft from a flight schedule information and so on maintained by airlines, airport companies, and so on and acquires a country of departure of the aircraft. The server apparatus 10 may determine a retention period of biometric information regarding a photographed person according to a country of departure. For example, the server apparatus 10 sets a longer retention period with regard to those who enter a country from countries where an infectious disease is prevalent. Alternatively, the server apparatus 10 may acquire travel information of a passenger through biometric authentication based on a face image of the passenger and identify a travel route (a country of departure) based on the acquired travel information. In order to identify the above travel route of the passenger, the server apparatus 10 may acquire information in which a face image and travel information are linked from a departure airport of the passenger (a server installed at the departure airport).

In the flowcharts and sequence diagrams used in the above description, a plurality of steps (processes) are sequentially described. However, the order of the execution of the steps performed in the individual example embodiment is not limited to the described order. In the individual example embodiment, the order of the illustrated steps may be changed to the extent that a problem is not caused on the content of the individual example embodiment. For example, individual processes may be executed in parallel.

The above example embodiments have been described in detail to facilitate the understanding of the present application disclosed and not to mean that all the configurations described above are needed. In addition, if a plurality of example embodiments has been described, each of the example embodiments may be used individually or a plurality of example embodiments may be used in combination. For example, part of a configuration according to one example embodiment may be replaced by a configuration according to another example embodiment. For example, a configuration according to one example embodiment may be added to a configuration according to another example embodiment. In addition, addition, deletion, or replacement is possible between part of a configuration according to one example embodiment and another configuration.

The industrial applicability of the present invention has been made apparent by the above description. That is, the present invention is suitably applicable, for example, to fever guide systems at airports.

A part or the entirety of the example embodiments described above may be described as in the following supplementary notes, but is not limited to the followings.

[Supplementary Note 1]

A server apparatus, includes:
    a registration unit that acquires thermal image data representing a thermal distribution of a first location and first image data photographed at the first location from a first camera device installed at the first location, determines whether or not a first person passing through the first location is a person with fever based on the thermal image data, acquires biometric information of the person with fever from the first image data, and registers the biometric information of the person with fever in a fever information database;
    a detection unit that acquires second image data photographed at a second location from a second camera device installed at the second location, and detects the person with fever at the second location using biometric information of a second person in the second image data and the biometric information registered in the fever information database; and a notification unit that transmits a fever detection notification, the fever detection notification including biometric information of the detected person with fever, to a terminal owned by a staff member to guide the person with fever to a third location.

[Supplementary Note 2]

The server apparatus according to supplementary note 1, wherein the registration unit determines whether or not the first person is the person with fever based on a number of pixels in the thermal image data whose pixel values is equal to or greater than a predetermined value.

[Supplementary Note 3]

The server apparatus according to supplementary note 1 or 2, wherein the detection unit detects the person with fever at the second location by one-to-N matching (N is a positive integer) using biometric information of the second person in the second image data and biometric information registered in the fever person information database.

[Supplementary Note 4]

The server apparatus according to any one of supplementary notes 1 to 3, further including a guide unit that guides the person with fever at the second location to the third location.

[Supplementary Note 5]

The server apparatus according to supplementary note 4, wherein the second camera device transmits two pieces of the second image data with different shooting directions, and wherein the guide unit identifies a location of the person with fever at the second location based on the two pieces of the second image data with different shooting directions, and displays a message at the identified location to direct the person with fever to the third location.

[Supplementary Note 6]

The server apparatus according to any one of supplementary notes 1 to 5, wherein the first camera device is installed to be able to photograph passengers passing through a corridor that connects a runway where an airplane lands and an airport terminal, and wherein the second camera device is installed to be able to photograph passengers heading to an immigration examination area passing through the airport terminal.

[Supplementary Note 7]

The server apparatus according to any one of supplementary notes 1 to 6, wherein a photographable range of the second camera device is wider than a photographable range of the first camera device.

[Supplementary Note 8]

The server apparatus according to any one of supplementary notes 1 to 7, wherein the third location is a location for inspecting the person with fever.

[Supplementary Note 9]

The server apparatus according to any one of supplementary notes 1 to 8, wherein the biometric information is a face image or a feature value generated from the face image.

[Supplementary Note 10]

A system, including:
a first camera device installed at a first location;
a second camera device installed at a second location;
a terminal owned by a staff member; and
a server apparatus connected to the first camera device, the second camera device and the terminal, wherein the server apparatus includes:
a registration unit that acquires thermal image data representing a thermal distribution of a first location and first image data photographed at the first location from a first camera device installed at the first location, determines whether or not a first person passing through the first location is a person with fever based on the thermal image data, acquires biometric information of the person with fever from the first image data, and registers the biometric information of the person with fever in a fever information database;

a detection unit that acquires second image data photographed at the second location from the second camera device, and detects the person with fever at the second location using biometric information of a second person in the second image data and the biometric information registered in the fever information database; and a notification unit that transmits a fever detection notification, the fever detection notification including biometric information of the detected person with fever, to a terminal owned by a staff member to guide the person with fever to a third location.

[Supplementary Note 11]

The system according to supplementary note 10, further including:
a gate apparatus that examines whether or not a user is permitted to pass through a gate, wherein the registration unit transmits the registered biometric information of the person with fever to the gate apparatus when registering the biometric information of the person with fever in the fever information database, and wherein the gate apparatus determines whether or not a person to be examined is the person with fever using transmitted biometric information of the person with fever and denies the person to be examined to pass through the gate when the person to be examined is the person with fever.

[Supplementary Note 12]

The system according to supplementary note 11, wherein the gate apparatus carries out immigration examination of the user.

[Supplementary Note 13]

A control method of a server apparatus, the control method including:
acquiring thermal image data representing a thermal distribution of a first location and first image data photographed at the first location from a first camera device installed at the first location;

determining whether or not a first person passing through the first location is a person with fever based on the thermal image data;

acquiring biometric information of the person with fever from the first image data, and registering the biometric information of the person with fever in a fever information database;

acquiring second image data photographed at a second location from a second camera device installed at the second location;

detecting the person with fever at the second location using biometric information of a second person in the second image data and the biometric information registered in the fever information database; and transmitting a fever detection notification, the fever detection notification including biometric information of the detected person with fever, to a terminal owned by a staff member to guide the person with fever to a third location.

[Supplementary Note 14]

A computer-readable storage medium storing a program causing a computer mounted on a server apparatus to perform processing for:
 acquiring thermal image data representing a thermal distribution of a first location and first image data photographed at the first location from a first camera device installed at the first location;
 determining whether or not a first person passing through the first location is a person with fever based on the thermal image data;
 acquiring biometric information of the person with fever from the first image data, and registering the biometric information of the person with fever in a fever information database;
 acquiring second image data photographed at a second location from a second camera device installed at the second location;
 detecting the person with fever at the second location using biometric information of a second person in the second image data and the biometric information registered in the fever information database; and
 transmitting a fever detection notification, the fever detection notification including biometric information of the detected person with fever, to a terminal owned by a staff member to guide the person with fever to a third location.

The entire disclosure of the above patent literature is incorporated herein by reference thereto. While the example embodiments of the present invention have thus been described, the present invention is not limited to these example embodiments. It is to be understood to those skilled in the art that these example embodiments are only examples and that various variations are possible without departing from the scope and sprit of the present invention. That is, the present invention of course includes various variations and modifications that could be made by those skilled in the art in accordance with the overall disclosure including the claims and the technical concept.

REFERENCE SIGNS LIST 100 server apparatus
20-1 to 20-3 first camera device
30 second camera device
40 terminal
50, 50-1, 50-2 gate apparatus
101 registration unit
102 detection unit
103 notification unit
201, 301 communication control unit
202 fever registration unit
203 fever detection unit
204 fever notification unit
205, 305 storage unit
206 fever guide unit
302 list generation unit
303 immigration examination unit
304 gate control unit
311 processor
312 memory
313 input-output interface
314 communication interface

What is claimed is:

1. A server apparatus, comprising:
 at least one memory storing a set of instructions; and
 at least one processor configured to execute the set of instructions to:
 acquire thermal image data representing a thermal distribution of a first location and first image data photographed at the first location from a first camera device installed at the first location, determine whether or not a first person passing through the first location is a person with fever based on the thermal image data, acquire biometric information of the person with fever from the first image data, and register the biometric information of the person with fever in a fever information database;
 acquire second image data photographed at a second location from a second camera device installed at the second location, and detect the person with fever at the second location using biometric information of a second person in the second image data and the biometric information registered in the fever information database;
 and transmit a fever detection notification, the fever detection notification including biometric information of the detected person with fever, to a terminal owned by a staff member to guide the person with fever to a third location; and
 detects the person with fever at the second location by one-to-N matching (N is a positive integer) using biometric information of the second person in the second image data and biometric information registered in the fever person information database,
 wherein the second camera device transmits two pieces of the second image data with different shooting directions, and
 wherein
 the at least one processor is further configured to execute the set of instructions to:
 identify the guide unit identifies a location of the person with fever at the second location based on the two pieces of the second image data with different shooting directions, and displays a message at the identified location to direct the person with fever to the third location.

2. The server apparatus according to claim 1, wherein the at least one processor is further configured to execute the set of instructions to:
 determine whether or not the first person is the person with fever based on a number of pixels in the thermal image data whose pixel values is equal to or greater than a predetermined value.

3. The server apparatus according to claim 1, wherein the at least one processor is further configured to execute the set of instructions to:
 guide the person with fever at the second location to the third location.

4. The server apparatus according to claim 1, wherein the first camera device is installed to be able to photograph passengers passing through a corridor that connects a runway where an airplane lands and an airport terminal, and
 wherein the second camera device is installed to be able to photograph passengers heading to an immigration examination area passing through the airport terminal.

5. The server apparatus according to claim 1, wherein a photographable range of the second camera device is wider than a photographable range of the first camera device.

6. The server apparatus according to claim 1, wherein the third location is a location for inspecting the person with fever.

7. The server apparatus according to claim 1, wherein the biometric information is a face image or a feature value generated from the face image.

8. A system, comprising:
a first camera device installed at a first location;
a second camera device installed at a second location;
a terminal owned by a staff member; and
a server apparatus connected to the first camera device, the second camera device and the terminal,
wherein the server apparatus includes:
at least one memory storing a set of instructions; and
at least one processor configured to execute the set of instructions to:
acquire thermal image data representing a thermal distribution of a first location and first image data photographed at the first location from a first camera device installed at the first location, determine whether or not a first person passing through the first location is a person with fever based on the thermal image data, acquire biometric information of the person with fever from the first image data, and register the biometric information of the person with fever in a fever information database;
acquire second image data photographed at the second location from the second camera device, and detect the person with fever at the second location using biometric information of a second person in the second image data and the biometric information registered in the fever information database;
and transmit a fever detection notification, the fever detection notification including biometric information of the detected person with fever, to a terminal owned by a staff member to guide the person with fever to a third location; and
detects the person with fever at the second location by one-to-N matching (N is a positive integer) using biometric information of the second person in the second image data and biometric information registered in the fever person information database,
wherein the second camera device transmits two pieces of the second image data with different shooting directions, and
wherein
the at least one processor is further configured to execute the set of instructions to:
identify a location of the person with fever at the second location based on the two pieces of the second image data with different shooting directions, and displays a message at the identified location to direct the person with fever to the third location.

9. The system according to claim 8, further comprising:
a gate apparatus that examines whether or not a user is permitted to pass through a gate,
wherein
the at least one processor is further configured to execute the set of instructions to:
transmit the registered biometric information of the person with fever to the gate apparatus when registering the biometric information of the person with fever in the fever information database, and
wherein the gate apparatus determines whether or not a person to be examined is the person with fever using transmitted biometric information of the person with fever and denies the person to be examined to pass through the gate when the person to be examined is the person with fever.

10. The system according to claim 9, wherein the gate apparatus carries out immigration examination of the user.

11. A control method of a server apparatus performed by a processor, the control method comprising:
acquiring thermal image data representing a thermal distribution of a first location and first image data photographed at the first location from a first camera device installed at the first location;
determining whether or not a first person passing through the first location is a person with fever based on the thermal image data;
acquiring biometric information of the person with fever from the first image data, and registering the biometric information of the person with fever in a fever information database;
acquiring second image data photographed at a second location from a second camera device installed at the second location;
detecting the person with fever at the second location using biometric information of a second person in the second image data and the biometric information registered in the fever information database;
and transmit a fever detection notification, the fever detection notification including biometric information of the detected person with fever, to a terminal owned by a staff member to guide the person with fever to a third location;
detects the person with fever at the second location by one-to-N matching (N is a positive integer) using biometric information of the second person in the second image data and biometric information registered in the fever person information database,
transmitting two pieces of the second image data with different shooting directions, and
identify a location of the person with fever at the second location based on the two pieces of the second image data with different shooting directions, and displays a message at the identified location to direct the person with fever to the third location.

* * * * *